United States Patent [19]
Saito et al.

[11] 3,959,339
[45] May 25, 1976

[54] PROCESS FOR PRODUCING AROMATIC NITRILES

[75] Inventors: Masao Saito; Mamoru Onozawa; Takamasa Kawakami, all of Niigata, Japan

[73] Assignee: Mitsubishi Gas Chemical Company, Inc., Tokyo, Japan

[22] Filed: June 4, 1974

[21] Appl. No.: 476,270

[30] Foreign Application Priority Data
June 5, 1973    Japan.............................. 48-63599

[52] U.S. Cl.............................. 260/465 C; 252/432
[51] Int. Cl.$^2$......................................... C07C 120/14
[58] Field of Search ................................ 260/465 C

[56] References Cited
UNITED STATES PATENTS
3,772,212    11/1973    Saito et al.................. 260/465 X R Primary Examiner—Lewis Gotts
Assistant Examiner—Dolph H. Torrence
Attorney, Agent, or Firm—Armstrong, Nikaido & Wegner

[57] ABSTRACT

Aromatic nitriles are produced in good yield from a gas mixture comprising alkyl-substituted aromatic compound, ammonia and molecular oxygen by ammoxidation by passing the gas mixture over a catalyst comprising vanadium oxide, chromium oxide, boron oxide and phosphorus oxide, deposited on a silica carrier, in an atomic ratio of V : Cr : B : P of 1 : 0.5 – 2.0 : 0.1 – 1.2 : 0.01 – 0.3 and a catalyst concentration of 20 to 80 % by weight at a reaction temperature of 300° to 500°C for a contact time of 0.5 to 30 seconds.

8 Claims, No Drawings

PROCESS FOR PRODUCING AROMATIC NITRILES

This invention relates to a catalyst for producing aromatic nitriles from a gas mixture containing alkyl-substituted aromatic compound, ammonia and molecular oxygen, more particularly a catalyst comprising vanadium oxide, chromium oxide, boron oxide and phosphorus oxide, deposited on a silica carrier, in an atomic ratio of vanadium : chromium : boron : phosphorus of 1 : 0.5 – 2.0 : 0.1 – 1.2 : 0.01 – 0.3, and also to a process for producing aromatic nitriles from a gas mixture containing alkyl-substituted aromatic compound, ammonia and molecular oxygen, using the catalyst of the present invention.

Heretofore, various catalysts and processes have been proposed for producing aromatic nitriles by reaction of alkyl-substituted aromatic compounds with ammonia, and molecular oxygen. Most of prior arts are based on catalysts of vanadium system. Single vanadium oxide catalyst is too strong in catalytic activity and relatively low in yield of aromatic nitriles, and therefore vanadium oxide catalysts containing various other metal oxides have been so far proposed. Among these catalysts there are those which can produce nitriles in considerable yield, but most of these catalysts require strict preparation conditions with poor reproducibility of the catalysts, or produce much by-products such as aromatic imides, amides, etc. or have a tendency to greatly reduce the yield of desired nitrile by a slight deviation from optimum conditions such as reaction temperature, contact time, etc. Furthermore, these catalysts are very liable to bring about formation reactions of coloring materials, hydrogen cyanide, carbon dioxide, carbon monoxide, etc. Therefore, much expense is incurred in their purification. Furthermore, there appear hot spots in catalyst layer or excessive decomposition of ammonia. These are the disadvantages of the prior art catalysts.

The present inventors previously found that these disadvantages were improved by using a catalyst comprising vanadium oxide, chromium oxide, and boron oxide, and yield of the desired nitrile could be considerably improved at the same time (Japanese Pat. No. 618714). Further, the present inventors found that, when silica was used as carriers, the catalyst had relatively high boron atomic ratio and catalyst concentration (Japanese Pat. application No. 40510/70).

Japanese laid-open Pat. application No. 34337/72 discloses that a catalyst comprising vanadium oxide, chromium oxide, and phosphorus oxide in an atomic ratio of vanadium : chromium : phosphorus of 1 : 0.1 – 10 : 0.1 – 5 has a good activity in producing aromatic nitriles.

The relevant catalytic reaction is a very vigorous exothermic reaction, and therefore it is very advantageous in removal of the heat of reaction and prevention of local superheating to carry out the reaction in a fluidized bed system. The catalysts applied to the fluidized bed reaction require good fluidizeability and attrition resistance, and a definite range of bulk density and particle size distribution as physical properties. The present inventors previously found that the desired physical properties could not be obtained when alumina was used as carriers, but could be obtained only when silica was used as carriers.

Therefore, it is necessary to use silica as the carriers, but when silica is used as the carriers for the three components, vanadium, chromium and phosphorus, yield of aromatic nitriles is lowered, and is rather lower than the yield in the case of the two-component catalyst of vanadium and chromium.

On the other hand, when the catalytic oxidation or ammoxidation is carried out in a fluidized bed system, occurrence of channeling due to the generation of bubbles or back-mixing due to movement of particles is inevitable, and consequently it is hard to attain 100% conversion, and a longer residence time of reactant gas than expected is required. That is, decomposition of reaction products increasingly takes place, and consequently the selectivity of the desired nitrile is lowered. To prevent these disadvantageous consequences, various modifications have been made of the type of reactor so as to make the occurrence of channeling or back-mixing as small as possible, and at the same time reaction conditions have been made severe, that is, the reaction temperature has been made higher to improve the conversion. However, in that case, the products are usually decomposed, and consequently the conversion is lowered.

Therefore, it is desirable to provide a catalyst, which will not lower the selectivity even at such a high reaction temperature, in other words, a catalyst showing a maximum yield in a broad range of temperatures.

An object of the present invention is to provide a catalyst that can meet said desirable requirements.

As a result of studies on the catalysts, the present inventors have found that, when the reaction is carried out in the presence of a catalyst comprising vanadium oxide, chromium oxide, boron oxide and phosphorus oxide, aromatic nitriles can be produced in very high yield for a prolonged period of time under very severe oxidation conditions in a wide range of temperatures and space velocities.

The present invention provides a catalyst for producing aromatic nitriles from a gas mixture containing alkyl-substituted aromatic compound, ammonia, and molecular oxygen, comprising vanadium oxide, chromium oxide, boron oxide and phosphorus oxide deposited on a silica carriers in an atomic ratio of vanadium : chromium : boron : phosphorus of 1 : 0.5 – 2.0 : 0.1 – 1.2 : 0.01 – 0.3, preferably 1 : 0.7 – 1.5 : 0.3 – 1.0 : 0.01 – 0.2 and having a catalyst concentration of 20 to 80 % by weight, preferably 30 to 60 % by weight. The catalyst concentration is a percent by weight of total oxides of vanadium, chromium, boron and phosphorus, in terms of $V_2O_5$, $Cr_2O_3$, $B_2O_3$ and $P_2O_5$, respectively, on the basis of the entire catalyst.

The present invention further provides a process for producing aromatic nitriles from a gas mixture containing alkyl-substituted aromatic compound ammonia and molecular oxygen, using the catalyst of the present invention.

According to the present invention, temperature control of catalyst bed can be much readily effected with very less occurrence of side reactions and a very wide range of optimum reaction temperatures. Space velocity can be varied in a broad range without any decrease in yield, and the yield of the desired nitrile can be further increased. Particularly even at a temperature higher than the temperature for maximum yield, the yield of nitrile is hardly lowered. This permits to reduce the amount of unreacted raw materials and the yield of reaction intermediates, and facilitate purification of the desired nitrile.

The present catalyst is applicable not only to a fluidized bed reaction, but also to a fixed bed reaction with its good catalyst characteristics.

As the raw materials for the catalyst components of the present catalyst, that is, vanadium oxide, chromium oxide, boron oxide and phosphorus oxide, these oxides can be used as such, or various oxides that can be readily converted to the corresponding oxides by proper treatments such as heating at the preparation of the catalyst, for example, such vanadium compounds as ammonium metavanadinate, vanadyl sulfate, vanadium salts of organic acids such as oxalic acid, tartaric acid, etc.; such chromium compounds as chromic acid, chromium nitrate, chromium hydroxide, ammonium chromate, ammonium bichromate, chromium salts of organic acids such as oxalic acid, tartaric acid, etc.; such boron compounds as boric acid and ammonium borate; such phosphorus compounds as phosphoric acid, ammonium phosphate, etc. can be used. As silica, silica sol is used.

The present catalyst can be prepared according to the well known procedure. For example, an aqueous boric acid solution and an aqueous phosphoric acid solution are added to a solution of vanadium oxide and chromium oxide in oxalic acid, and then silica sol is added thereto to obtain a slurry mixture. In that case, a dissolving agent for boric acid is used, if required. As the dissolving agent for boric acid, polyhydric alcohols, α-monohydroxycarboxylic acids and dihydroxycarboxylic acids are used. In the case of preparing fluidized bed catalysts, the slurry mixture is spray dried and then calcined. In the case of preparing fixed bed catalyst, the slurry mixture is evaporated to dryness, and then calcined. Calcination is carried out at a temperature of 400° to 700°C, preferably 450° to 650°C for more than a few hours, while passing air over the resulting residue.

As the alkyl-substituted aromatic compounds, toluene, ethylbenzene, polymethylbenzenes (xylene, mesitylene, cymene, durene, etc.), diethylbenzene, methylnaphthalene, etc. are used.

Concentration of the aromatic compound in the reactant gas is 0.5 to 5 % by volume, when air is used as an oxygen source.

The higher the concentration in volume of ammonia in the reactant gas than the theoretically required one, the higher the yield of nitriles from the aromatic compound. However, in view of recovery technology of unreacted ammonia, it is advantageous that the concentration in volume of ammonia is higher than the theoretically required one, preferably 2 to 10 times as high as the theoretically required one.

It is necessary that the concentration in volume of oxygen in the reactant gas is at least 1.5 times, preferably 2 to 50 times, as high as the theoretically required one. Air is usually used as an oxygen source, but it is possible to use nitrogen, carbon dioxide, steam, etc. as an inert diluent to the reactant gas.

Reaction is carried out at a temperature of 300° to 500°C, preferably 330° to 470°C. Conversion of the raw material aromatic compound is low below 300°C, and formation of carbon dioxide, hydrogen cyanide, etc. is increased above 500°C, resulting in decrease in the yield of nitriles. The reaction temperature showing a maximum yield depends upon kind and concentration of the raw material aromatic compound, contact time, etc., and therefore should be selected from said temperature range in view of the reaction conditions.

The contact time of the reactant gas with the catalyst can be made considerably longer, but preferable contact time is 0.5 to 30 seconds.

Generally, gaseous phase ammoxidation reaction of alkyl-substituted aromatic compound releases much heat, and the removal of the heat of reaction is an important problem. The present catalyst can greatly improve such a problem, and even in the fixed bed reaction, a temperature of the catalyst bed can be sufficiently kept in a desirable range. The use of fluidized bed type reaction or moving bed type reaction is, of course, more effective. The present catalyst has a good attrition resistance and fluidizeability as the fluidized bed catalyst.

The reaction is usually carried out in a pressure of 1 – 3 atm., but can be also carried out under more elevated pressure or reduced pressure.

For collection of the reaction products, any suitable procedure, for example, cooling the reaction product gas to a temperature enough to condense the product or scrubbing the reaction product gas with water or other suitable solvent, can be used.

Now, the present invention will be explained in detail, referring to examples.

Example 1

1000 ml of water is added to 618 g of oxalic acid, and 247 g of vanadium pentoxide is dissolved in the resulting solution, while heating the solution at 80° to 90°C.

271.5 g of chromic anhydride is dissolved in 500 ml of water, and then the resulting solution is added to a slurry prepared by adding 1048 g of oxalic acid to 1500 ml of water and heating the resulting mixture at 50° to 60°C. The resulting solution of vanadyl oxalate and that of chromium oxalate are mixed together, and the resulting mixture is concentrated by heating to a liquid volume of about 1500 ml. Then, 84 g of boric acid, 200 g of tartaric acid, and 4.7 g of 85 % phosphoric acid are added to the resulting concentrated solution, and well mixed. Then, 1667 g of 30 % aqueous silica sol is added to the resulting catalyst solution, and the resulting slurry mixture is spray dried, while keeping an inlet gas temperature and an outlet gas temperature at 250°C and 150°C, respectively. The resulting spray dried catalyst is dried in a drier at 250°C for 12 hours, and calcined at 550°C for 12 hours, while passing air over the catalyst. The resulting catalyst has an atomic ratio of V : Cr : B : P = 1 : 1 : 0.5 : 0.015, and a catalyst concentration of 50 % by weight. The catalyst is substantially in a spherical form, and have a bulk density of 0.95 g/ml and particle sizes of 20 to 150 microns.

40 ml of the catalyst is fed in a tubular reactor having an inner diameter of 23 mm, heated in a molten salt bath, and a gas consisting of 1.2 % by volume of paraxylene, 9.6 % by volume of ammonia and 89.2 % by volume of air is passed through the reactor at a reaction temperature of 395°C, an atmospheric pressure and a contact time of 6 seconds. As a result, terephthalonitrile and paratolunitrile are obtained in yields of 85.2 % by mole and 6.1 % by mole, respectively, on the basis of paraxylene. When the reaction temperature is further elevated to 425°C, terephthalonitrile and paratolunitrile are obtained in yields of 82.7 % by mole and 0.4 % by mole, respectively.

Example 2

When a gas consisting of 1.31 % by volume of toluene, 6.55 % by volume of ammonia and 92.14 % by mole of air is passed through the same reactor as used in Example 1 at a reaction temperature of 435°C, an atmospheric pressure and a contact time of 6 seconds, benzonitrile is obtained in yield of 85.2 % by mole, on the basis of toluene.

Example 3

A catalyst having an atomic ratio of V : Cr : B : P = 1 : 1 : 0.7 : 0.09 and a catalyst concentration of 50 % by weight is prepared in the same manner as in Example 1. The form, bulk density and particle sizes of the resulting catalysts are the same as those obtained in Example 1.

A gas consisting of 1.30 % by volume of metaxylene, 10.4 % by volume of ammonia and 88.3 % by volume of air is passed through a reactor containing 30 ml of the catalyst at a reaction temperature of 380°C, an atmospheric pressure and a contact time of 12 seconds, the reactor being the same as used in Example 1. As a result, isophthalonitrile and metatolunitrile are obtained in yields of 83.0 % by mole and 3.4 % by mole, respectively, on the basis of metaxylene. When the reaction temperature is further elevated to 430°C and the reaction is carried out for a contact time of 3 seconds, isophthalonitrile and metatolunitrile are obtained in yields of 82.1 % by mole and 0.3 % by mole, respectively.

Comparative Example 1

A catalyst having an atomic ratio of V : Cr = 1 : 1 and a catalyst concentration of 50 % by weight on silica carriers is prepared in the same manner as in Example 1. A gas consisting of 1.30 % by volume of metaxylene, 13.0 % by volume of ammonia and 85.7 % by volume of air is passed through a reactor containing 40 ml of the catalysts at a reaction temperature of 380°C, an atmospheric pressure and a contact time of 6 seconds. As a result, isophthalonitrile and metatolunitrile are obtained in yields of 59 % by mole and 3.0 % by mole, respectively, on the basis of metaxylene.

Comparative Example 2

A catalyst having an atomic ratio of V : Cr : P = 1 : 1 : 0.5 and a catalyst concentration of 50 % by weight on silica carriers is prepared in the same manner as in Example 1. The same gas as used in Comparative Example 1 is passed through a reactor containing 40 ml of the catalysts at a reaction temperature of 400°C, an atmospheric pressure and a contact time of 6 seconds. As a result, isophthalonitrile and metatolunitrile are obtained in yields of 54.0 % by mole and 7.0 % by mole, respectively, on the basis of metaxylene.

Japanese laid-open Pat. application No. 34337/72 discloses that a catalyst comprising vanadium oxide, chromium oxide and phosphorus oxide in atomic ratio of V : Cr : P = 1 : 0.1 – 10 : 0.1 – 5 is good catalyst for producing aromatic nitriles.

However, as shown in the foregoing Comparative Examples, addition of phosphorus to a two-components catalyst of vanadium and chromium based on silica carriers reduces the yield of nitrile, to the contrary.

What is claimed is:

1. A process for producing aromatic nitriles by ammoxidation, which comprises passing a gas mixture comprising alkyl-substituted aromatic compound, ammonia and molecular oxygen over a catalyst comprising vanadium oxide, chromium oxide, boron oxide and phosphorus oxide, deposited on a silica carrier, in an atomic ratio of V : Cr : B : P of 1 : 0.5 – 2.0 : 0.1 – 1.2 : 0.01 – 0.3 and a catalyst concentration of 20 to 80 % by weight at a reaction temperature of 300° to 500°C for a contact time of 0.5 to 30 seconds.

2. A process according to claim 1, wherein the catalyst has an atomic ratio of V : Cr : B : P of 1 : 0.7 – 1.5 : 0.3 – 1.0 : 0.01 – 0.2 and a catalyst concentration of 30 to 60 % by weight.

3. A process according to claim 1, wherein the gas mixture contains 0.5 to 5 % by volume of the aromatic compound when the molecular oxygen is in a form of air.

4. A process according to claim 1, wherein the gas mixture contains ammonia in volumes 2 to 10 times as much as theoretically required one.

5. A process according to claim 1, wherein the gas mixture contains molecular oxygen in volumes at least 1.5 times as much as theoretically required one.

6. A process according to claim 5, wherein the molecular oxygen is contained in volumes 2 to 50 times as much as theoretical.

7. A process according to claim 1, wherein the reaction temperature is 330° to 470°C.

8. A process according to claim 1, wherein the alkyl-substituted aromatic compound is toluene, ethylbenzene, xylene, mesitylene, cymene, durene, diethylbenzene or methylnaphthalene.

* * * * *